United States Patent [19]

Cooper et al.

[11] Patent Number: 4,757,381
[45] Date of Patent: Jul. 12, 1988

[54] MEANS AND STRUCTURE FOR PREVENTION OF CROSS CONTAMINATION DURING USE OF DENTAL CAMERA

[75] Inventors: David H. Cooper, Saratoga; Charles S. Bush, Los Gatos, both of Calif.

[73] Assignee: Fuji Optical Systems, Inc., Los Gatos, Calif.

[21] Appl. No.: 103,833

[22] Filed: Oct. 1, 1987

Related U.S. Application Data

[63] Continuation-in-part of Ser. No. 22,171, Mar. 5, 1987.

[51] Int. Cl.⁴ .............................................. A61B 1/04
[52] U.S. Cl. ...................... 358/98; 206/369; 206/63.5; 206/69; 358/229; 433/29
[58] Field of Search .................. 358/98, 229; 433/29, 433/30, 31; 128/4, 6, 132 D; 206/368, 369, 63.5, 69

[56] References Cited

U.S. PATENT DOCUMENTS

| 175,706 | 4/1876 | Howells | 433/30 |
|---|---|---|---|
| 2,332,857 | 10/1943 | Karg | 206/69 |
| 3,539,247 | 11/1970 | Broussard | 433/30 |
| 3,829,199 | 8/1974 | Brown | 433/30 |
| 3,884,222 | 5/1975 | Moore | 433/31 |
| 4,294,356 | 10/1981 | Abramowitz | 433/30 |
| 4,594,608 | 6/1986 | Hatae | 358/93 |

Primary Examiner—Howard W. Britton
Attorney, Agent, or Firm—Steven F. Caserza

[57] ABSTRACT

A sheath is provided which prevents the dental camera itself from coming into contact with the patient, while allowing the dental camera to function properly. Such sheaths are dispensed on a perforated role, either end to end, or side to side. Alternatively, each sheath is individually packaged in a tear away casing, allowing the sheath to remain sterile, yet being readily accessible for use.

20 Claims, 2 Drawing Sheets

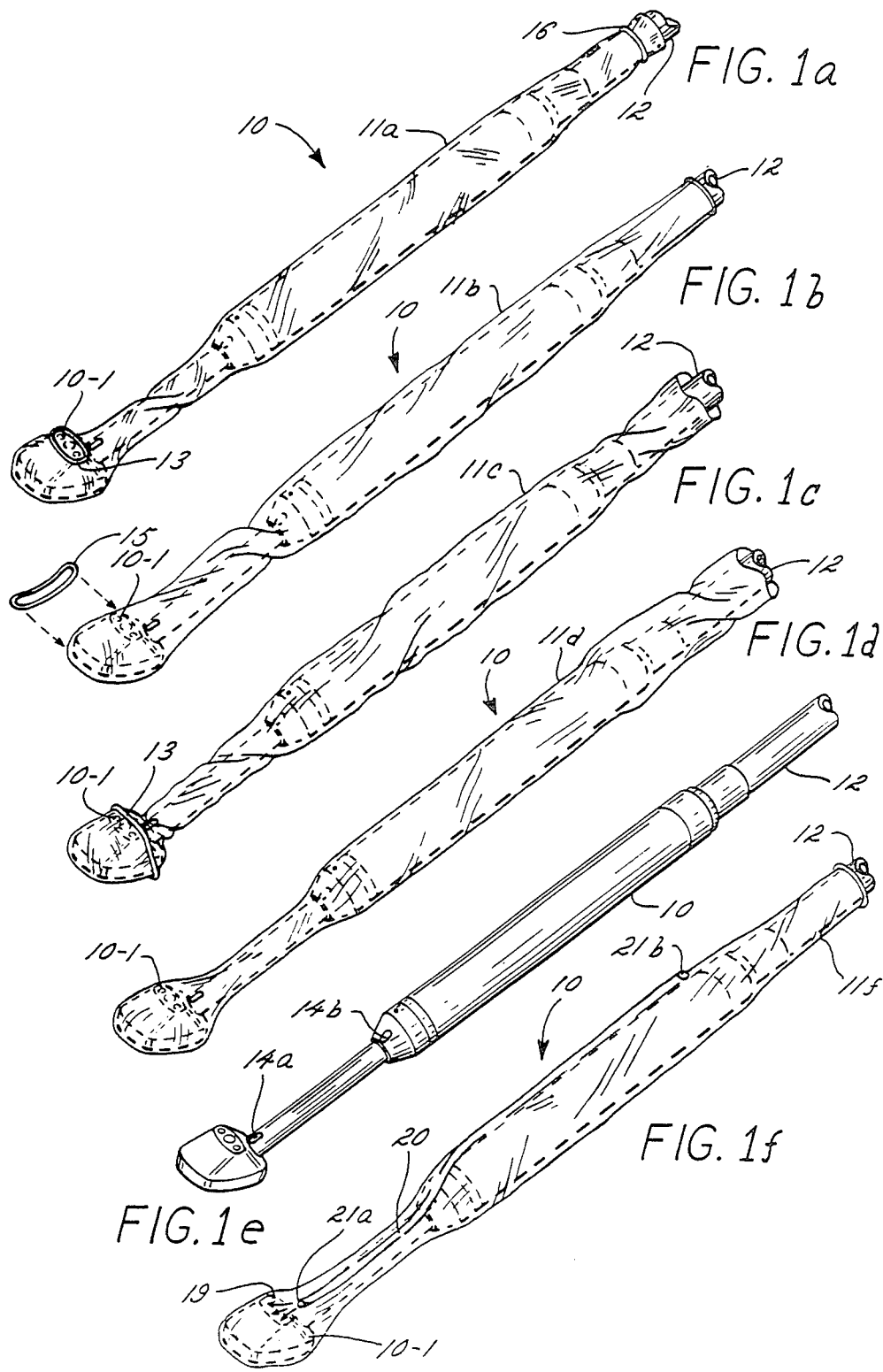

MEANS AND STRUCTURE FOR PREVENTION OF CROSS CONTAMINATION DURING USE OF DENTAL CAMERA

RELATED APPLICATIONS

This is a continuation-in-part of U.S. Ser. No. 22,171, filed Mar. 5, 1987, assigned to Fuji Optical Systems, Inc., the assignee of this invention.

BACKGROUND

This invention relates to a method and structure for the prevention of cross contamination during use of dental cameras.

For years, dentists have used dental mirrors for insertion in a dental patient's mouth for reflecting images of areas within the patients' mouth for viewing by the dentist. This technique works, although it has several disadvantages. First, it is often difficult to hold the dental mirror in an appropriate position in order to reflect the desired image. Secondly, it is more difficult to ensure that proper lighting is available to the area within the mouth to be reflected by the dental mirror. An even greater disadvantage is that it is very difficult to use such prior art dental mirrors in a situation where a dentist wishes to discuss certain regions within the mouth with other people, be it the patient, colleagues, dental assistants, or students in a teaching institution.

More recently, an electronic video dental camera has been taught, for example in U.S. patent application for an invention entitled "Electronic Video Dental Camera" (Ser. No. 22,171). When using dental tools, including such a dental camera, it is necessary to present to the patient at least a completely clean surface and, under certain conditions, a sterile surface. This is even more serious than might be generally realized, since often even minor dental procedures result in some degree of bleeding and therefore there is a danger of transmission of Hepatitis B and AIDS, for example, if such a dental camera is not sterilized between dental procedures among patients. In the instance of a dental camera, such cleaning or sterilization must be of not only of the camera head, but the handle and a suitable length of cable, as well.

One prior art technique for sterilizing or cleaning medical instruments is the submersion of the instrument in a liquid bath containing a suitable sterilizing or disinfecting agent, such as Sporicidin.

Oftentimes, liquid sterilization takes an inordinant amount of time, thereby not allowing a particular piece of medical equipment to be readily reused on another patient. A common solution to this problem is the acquisition of numerous pieces of the same type of equipment, thereby allowing use of one instrument while others are being sterilized. For example, it is quite common for a typical dentist's office to have numerous dental mirrors, and numerous dental picks of the same type, in order for one set of dental instruments to be in use on a patient, while others are being sterilized.

However, this presents a more significant problem when the device to be sterilized is more complex and expensive. Thus, prior art sterilization procedures for complex and expensive pieces of equipment leave much to be desired.

SUMMARY

In accordance with the teachings of this invention, a novel technique is provided for, in effect, providing a sterile dental camera. In accordance with the teachings of this invention, a sheath is provided which prevents the dental camera itself from coming into contact with the patient, while allowing the dental camera to function properly. In one embodiment of this invention, such sheaths are dispensed on a perforated roll, either end to end, or side to side. In another embodiment of this invention, each sheath is individually packaged in a tear away casing, allowing the sheath to remain sterile, yet being readily accessible for use.

BRIEF DESCRIPTION OF THE DRAWING

FIG. 1a through 1d illustrate embodiments of a sheath suitable for covering a dental camera, such sheaths being constructed in accordance with the teachings of this invention;

FIG. 1e shows a dental camera modified to include insufflation-aspiration channels for use in accordance with a sheath constructed in accordance with the teachings of this invention;

FIG. 1f is a diagram of another sheath constructed in accordance with the teachings of this invention which includes a fluid channel for providing fluid to the face of the dental camera;

DETAILED DESCRIPTION

Figure 2A:
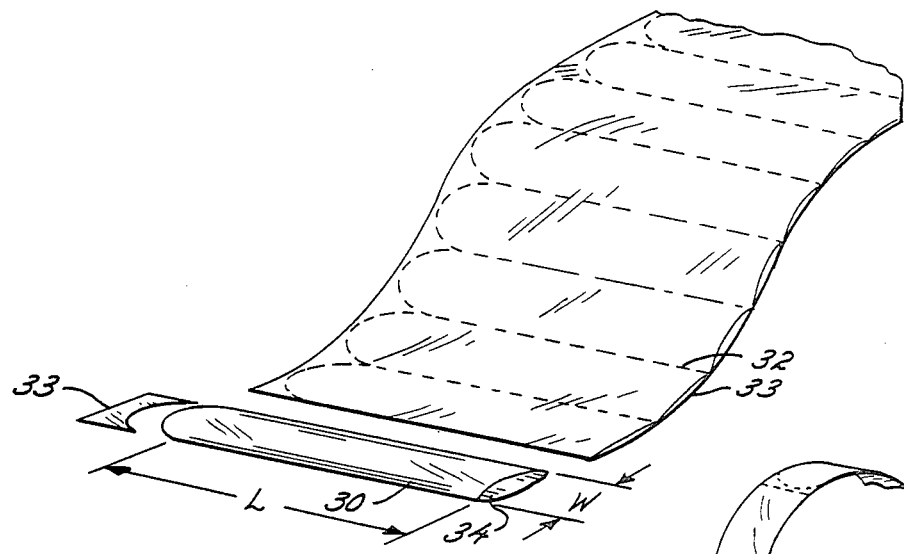
FIGS. 2a and 2b depict embodiments of dental sheaths of this invention wherein the dental sheaths are provided in perforated relationship to each other.

FIG. 1a is a drawing depicting one embodiment of a dental sheath constructed in accordance with the teachings of this invention. As shown in FIG. 1a, dental sheath 11a serves to cover dental camera 10 and, if desired, a selected length of cable 12 protruding from the proximal end of dental camera 10. In one embodiment of this invention, sheath 11a serves to cover approximately 6 to 12 inches of cable 12. In the embodiment of FIG. 1a, sheath 11a includes window 13 which serves to cover the lens portion of the dental camera head 10-1 such that sheath 11a does not significantly impede the transmission of light to and from the camera head 10-1 of dental camera 10. In this embodiment, sheath 11a is manufactured with, for example, a flexible rubber or plastic material, such as polyethylene or latex and window 13 is formed of, for example, clear acrylic. If desired, an elastic band, clip, or similar structure 16 is used in this or the following embodiments to secure the open end of sheath 11a to dental camera 10 or cable 12.

FIG. 1b shows an alternative embodiment of a dental sheath constructed in accordance with the teachings of this invention. Dental sheath 11b is formed of a thin material, such as mylar or clear polyethylene, which if desired fits rather loosely over dental camera 10 and a desired length of cable 12. Used in conjunction with dental sheath 11b is a fastening means 15, which might comprise an elastic band, clip, or similar structure, which serves to tighten and flatten dental sheath 11b, at least over camera head 10-1. In this manner, using suitable material to fabricate sheath 11b or at least that portion of sheath 116 which is placed over the lens of camera head 10-1, when tightened and flattened, becomes substantially transparent, thereby providing good transmissivity of light to and from the lens of camera head 10-1.

Another embodiment of a dental sheath constructed in accordance with the teachings of this invention is shown in FIG. 1c. In FIG. 1c, dental sheath 11c is a rather loosely fitting sheath for covering dental camera 10 and if desired a portion of cable 12. Operating in conjunction with sheath 11c is shoe 13 which serves to cover camera head 10-1 while providing a substantially transparent cover above the lens of camera head 10-1. Shoe 13 can be placed on camera head 10-1 either before or after sheath 11c is placed on dental camera 10.

Shown in FIG. 1d is an alternative embodiment of a sheath constructed in accordance with the teachings of this invention. As shown in FIG. 1d, sheath 11d is originally a rather loosely fitting sheath which is then shrunk around the distal end of dental camera 10 so as to provide a tight fit on camera head 10-1, thereby providing a substantially transparent covering for camera head 10-1. If desired, polyethylene is used to form dental sheath 11d or at least that portion of dental sheath 11d which is to be shrunk upon the application of heat.

FIG. 1e shows an embodiment of a dental camera 10 constructed in accordance with the teachings of this invention which includes one or more openings 14a and 14b to one or more insufflation-aspiration channels (not shown) located within dental camera 10. Openings 14a and 14b may be located at any convenient location on dental camera 10 and serve to provide a desired pressure for use in conjunction with a sheath as taught by this invention. For example, openings 14a and 14b can serve to provide either or both a slight pressure to moderately inflate a dental sheath as it is being placed on or removed from dental camera 10, and a slight vacuum in order to cause the dental sheath to properly adhere to dental camera 10, thereby preventing the sheath from sliding off the dental camera in use, and also for providing a tight fit of the sheath around camera head 10-1 thereby to provide a substantially transparent fit. If desired, the proximal end of the sheath can be held with a suitable means, such as an elastic band, tie fastener, or twist tie, or a similar structure fabricated in the sheath itself, in order to properly seal the open end of the sheath in order to allow the pressure provided by the insufflation-aspiration channnel to work to its utmost advantage.

FIG. 1f shows another embodiment of a dental sheath constructed in accordance with the teachings of this invention in which dental sheath 11f includes fluid channel 20 having an opening 21b for receiving fluid and an opening 21a for providing this fluid on the portion of dental sheath 11f which covers lens 19 of camera head 10-1. This fluid serves to minimize defogging and serves to cleanse the area above the camera lens, thereby permitting the appropriate transmission of light to and from the camera head.

Alternative methods for minimizing fogging are available in accordance with the teachings of this invention. For example, using suitable materials for the construction of the sheath itself, or the portion of the sheath which covers the camera head, will in itself minimize fogging since the surface of appropriate materials will rapidly assume ambient temperature. Alternatively, a portion of the dental camera sheath which covers the camera head can be sprayed or dipped in a sterile silicon compound in order to inhibit condensation and thereby prevent fogging. Other such sterile compounds can be used as well.

FIG. 2a depicts one emodiment of the construction of dental sheaths in accordance with the teachings of this invention for handy dispensing. As shown in FIG. 2a, a quantity of dental sheaths are provided in a roll or fanfold arrangement, for example, with individual dental camera sheaths in roll 31 being joined to adjacent sheaths via perforations 32. Thus, a user need only tear off an individual dental sheath 30 from roll 31 when it is desired to be used, much in the same way as a paper towel is torn from a roll of paper towels. If desired, an end portion 33 can be discarded after being torn by perforations holding it to dental sheath 34. End portion 33 serves to allow a rectangular stock to be used to form roll 31. As shown in FIG. 2a, dental camera sheath 30 includes opening 34 for entry of the dental camera. Dental camera sheath 30 would preferably have a length L within the range of 1 to 48 inches and a width W in the range of approximately 0.1 to 3 inches.

Figure 2B:
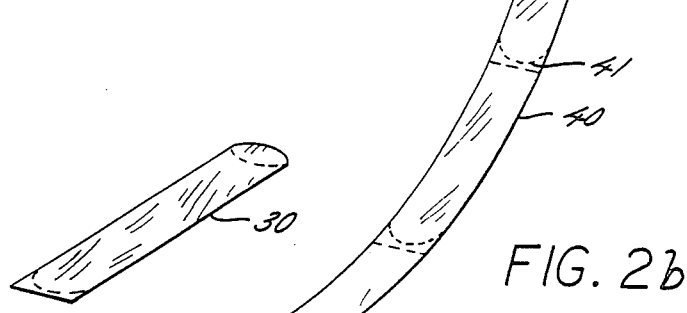

FIG. 2b depicts another convenient method for dispensing dental camera sheaths in accordance with the teachings of this invention. In FIG. 2b, a long tube-like material 40 is machined in order to have perforations 41 for separating longitudinally spaced adjacent dental sheaths. Preferably, simultaneously with the formation of perforations 41, one end of a dental sheath is sealed in order to provide a dental sheath having only one opening.

Figure 2C:
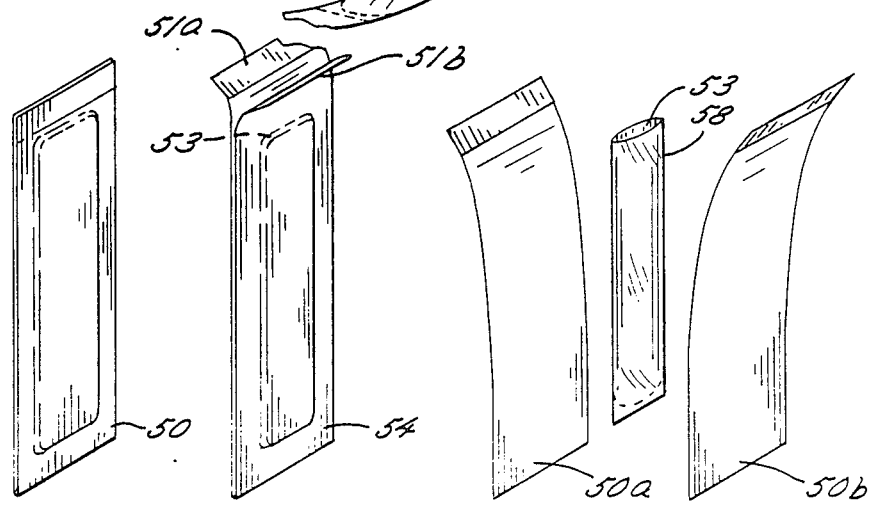
FIG. 2c depicts another embodiment of a means for packaging a dental sheath constructed in accordance with the teachings of this invention.

FIG. 2c depicts an alternative method for packaging dental sheaths. FIG. 2c shows a dental sheath package 50 including body portion 54 and foldable flaps 51a and 51b. In use, foldable flaps 51a and 51b are opened slightly, thereby exposing opening 53 of dental camera sheath 58. The dental camera can be inserted into opening 53 at this time, if desired, allowing the insertion to be performed without requiring any physical contact with the exterior of the dental sheath itself, since it is still protected by package body 54. Once the dental camera is inserted, flaps 51a and 51b are pulled and body 54 is split along its seams and peels away from dental camera sheath 58. This embodiment has the advantage of providing a sterile, individually packaged dental sheath which is readily available for use.

All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A dental camera sheath comprising:
   an opening at a first end for entry and exit of a dental camera;
   a distal end portion adapted to cover a camera head of said dental camera; and
   a window portion of said distal portion, said window portion being substantially transparent over a camera lens of said camera head.

2. A dental camera sheath as in claim 1 wherein said window portion comprises optically transparent material.

3. A dental camera sheath as in claim 1 wherein that portion other than said window portion comprises flexible rubber or plastic material.

4. A dental camera sheath as in claim 1 which further comprises a fluid channel for directing fluid to or from said window portion.

5. Means for dispensing dental camera sheaths as in claim 1 comprising:
   a plurality of said dental camera sheaths, each joined in a perforated relation along a longitudinal edge to an adjacent one of said dental camera sheaths.

6. Means for dispensing dental camera sheaths as in claim 1 comprising:
   a plurality of said dental sheaths joined end to end in a perforated relation.

7. A dental camera sheath as in claim 1 further comprising packaging means housing said sheath in a sterile environment, said packaging means including two mating portions for enclosing said sheath within, each of said portions including a foldable flap for grasping and peeling apart said mating portions, thereby removing said sheath from said packaging means.

8. A dental camera sheath as in claim 1 which further comprises means for fixing said distal portion in tight, bonding relation to said camera head.

9. A dental camera sheath as in claim 8 wherein said means for fixing comprises an elastic band or clip.

10. A dental camera sheath as in claim 1 which further comprises means for fixing said first end.

11. A dental camera sheath as in claim 10 wherein said means for fixing comprises an elastic band or clip.

12. A dental camera sheath as in claim 1 wherein said distal portion is capable of being shrunk-fit to said camera head.

13. A dental camera sheath as in claim 12 wherein said distal portion is shrunk by the application of heat.

14. A dental camera sheath as in claim 1 which further comprises a shoe for covering said distal portion, thereby holding said distal portion in tight, bonding relation to said camera head.

15. A dental camera sheath as in claim 14 wherein said shoe is substantialy transparent above said camera lens.

16. A dental camera sheath as in claim 15 wherein said shoe comprises optically transparent material.

17. A dental camera for use in displaying an image from inside the mouth of a monitor comprising an electronic video endoscope having a shape like a dental mirror, said endoscope comprising:
   a handle;
   a camera head including a camera lens located at the distal end of said handle, said camera head being formed such that said camera lens is placed at an angle from the axis of said handle; and
   a sheath covering said handle and camera head, said sheath being substantially transparent over said camera lens.

18. A dental camera as in claim 17 which further includes an insufflation/aspiration channel having at least one opening on a surface of said handle and camera head.

19. A dental camera as in claim 18 wherein said sheath is drawn to said handle and camera head in response to a vacuum applied to said channel.

20. A dental camera as in claim 18 wherein said sheath is pushed away from said handle and camera head in respsonse to a positive pressure applied to said channel.

* * * * *